United States Patent [19]

Nevens et al.

[11] Patent Number: 5,226,897
[45] Date of Patent: Jul. 13, 1993

[54] MANUALLY DRIVEN PISTON SYRINGE WITH FRANGIBLY MOUNTED TUBE ADAPTER

[75] Inventors: Charles Nevens; Edward Ferreri, both of Ocala, Fla.

[73] Assignee: Professional Medical Products, Inc., Greenwood, S.C.

[21] Appl. No.: 843,726

[22] Filed: Feb. 28, 1992

[51] Int. Cl.⁵ .................. A61M 5/315; A61M 5/30
[52] U.S. Cl. .................... 604/218; 604/227; 604/243
[58] Field of Search .......... 604/110, 193–195, 604/218, 220, 225, 226, 227, 240–243

[56] References Cited

U.S. PATENT DOCUMENTS

| | | | |
|---|---|---|---|
| 1,589,046 | 6/1926 | Brix | 604/227 |
| 2,842,128 | 7/1958 | Hein, Jr. | 604/227 |
| 3,161,195 | 12/1964 | Taylor et al. | 604/226 X |
| 3,220,413 | 11/1965 | Sunnen | 604/218 |
| 3,388,941 | 6/1968 | Marcus | 604/227 X |
| 3,845,763 | 11/1974 | Cloyd | 604/227 X |
| 4,246,898 | 1/1981 | Travalent et al. | 604/220 X |
| 4,386,606 | 6/1983 | Tretinyak et al. | 604/220 |
| 4,516,969 | 5/1985 | Kintner | |
| 4,636,202 | 1/1987 | Lowin et al. | |
| 4,919,652 | 4/1990 | Alter et al. | 604/110 |
| 4,925,449 | 5/1990 | Saez et al. | 604/227 |
| 4,929,238 | 5/1990 | Baum | |

FOREIGN PATENT DOCUMENTS 2648715 12/1990 France.

Primary Examiner—John D. Yasko
Assistant Examiner—Adam J. Cermak
Attorney, Agent, or Firm—Bell, Seltzer, Park & Gibson

[57] ABSTRACT

A syringe for controlled discharge and collection of fluids. The syringe includes a body having a hollow barrel, a first end with an opening for receiving a piston, and a second end having a nozzle. Flanges protrude from the first end of the body for manual engagement by a user. A piston having a longitudinal shaft is slidably received within the barrel. A first end of the piston has a gasket for slidably engaging the barrel to form a low pressure seal. A ring extends from the second end of the piston and defines a hollow receptacle for engagement by a user's thumb so that the piston may be urged into or withdrawn from the barrel. The ring has a broad flattened segment for supporting the syringe in an inverted position when the ring is placed on a horizontal surface. A tube adapter is provided on a frangible mounting on arms between the ring and piston shaft. A hole is provided in the piston for storing the tube adapter when it is not in use.

12 Claims, 2 Drawing Sheets

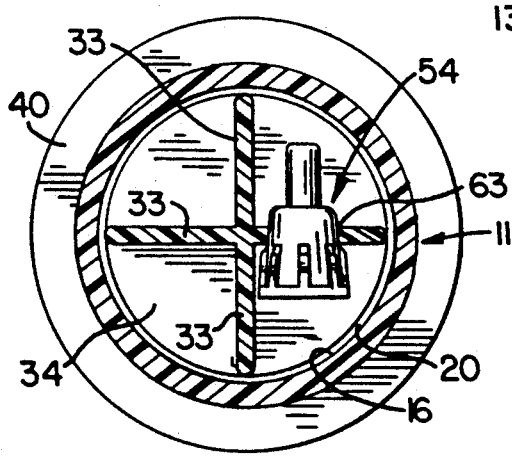
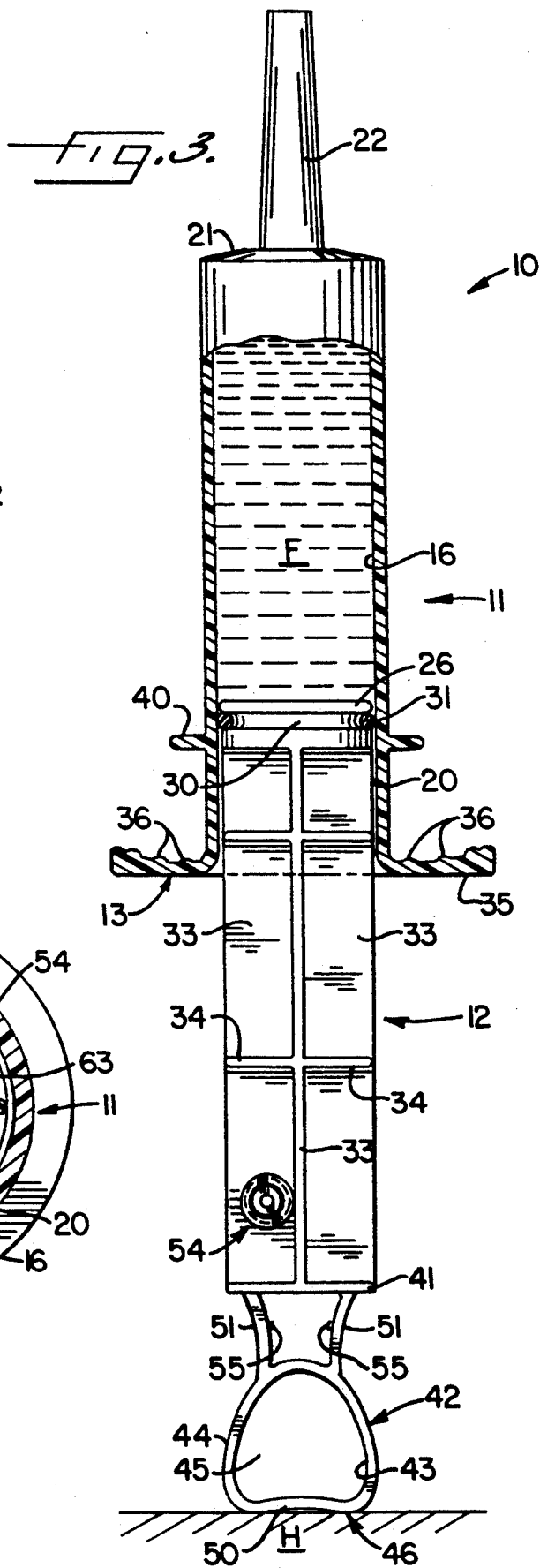

MANUALLY DRIVEN PISTON SYRINGE WITH FRANGIBLY MOUNTED TUBE ADAPTER

FIELD OF THE INVENTION

The present invention relates to piston syringes of the type frequently used for controlled discharge or collection of fluids. In particular, the invention relates to a piston syringe that may be used in medical applications to irrigate tissues or apply medicaments directly or through tubing.

BACKGROUND OF THE INVENTION

Piston syringes are commonly used in medical applications and in other environments to discharge or collect a variety of fluids. Frequently, piston syringes are used to irrigate tissues with saline solutions, and may also be used to administer medicaments or to administer nutrients to a patient. The syringes are also used to remove fluids that may have collected within tissues.

To achieve the foregoing and other functions, piston syringes generally have a relatively large capacity barrel within which a piston is slidably received. A user may move the piston within the syringe body to vary the void volume within the syringe body to discharge or collect fluids. Thus, by urging the piston into the syringe barrel, an operator may eject fluids from the syringe to irrigate tissues or other applications. Conversely, retracting the piston from the syringe barrel increases the volume of the void area, thereby causing a suction that draws fluids into the syringe barrel.

As a practical matter, health professionals who need to operate the piston syringe are often engaged in many activities simultaneously, thereby leaving them only one hand available to operate the syringe. This is especially true when the syringe is being used during surgery or in an emergency room. To facilitate easy manipulation, many piston syringes have a handle comprising opposed flanges extending from the upper portion of the syringe body that may be gripped by two fingers of a user's hand. A handle is attached to the upper end of the piston to enable the user to push the piston into the syringe body or to retract the piston. In most syringes that have been heretofore known, the underside of the opposed extending flanges on the syringe body may be gripped with the index and third or ring fingers, whereas the handle on the piston is usually engaged by the thumb. Of course, the piston may be urged into the syringe body easily enough by pushing the piston with the thumb; however, it may be cumbersome to retract the piston from the syringe body in order to collect fluids, and use of a second hand may be necessary.

Piston syringes are often used during surgery or other complex procedures. To expedite these procedures, it is desirable that the syringe be filled with a desired fluid prior to use and stored on a cart or table within easy reach of the anticipated user. It has been found to be particularly convenient to fill the syringe with a desired fluid and to position the syringe on the handle portion of the piston, which must be partially extended from the syringe body so that the syringe may accommodate the fluid. When the syringe is so positioned, it rests on the table or cart in a substantially inverted position. In this way, a completely filled syringe may be set aside without leaking the fluid contained therein.

In many cases, it is necessary to use piston syringes in conjunction with tubing that extends to a piece of equipment or to a patient's body. Syringes are often connected to tubing of various sizes when it is necessary to irrigate a distant portion of a patient's body, to administer a medicament or food, or when the syringe is used in conjunction with other apparatus. Accordingly, it has been found desirable to provide the syringe with a nozzle that may be mated with the tubing. However, because different sizes of tubing may be used for different purposes, it has been found desirable to provide the syringe with an adapter which may be fitted to the nozzle in order to accommodate a relatively larger or smaller size of tubing than would otherwise be possible.

The tube adapters are usually quite small and are apt to be misplaced, particularly in a hectic work environment. Thus, it is desirable to provide the syringe with such an adapter. It is also desirable to provide means for storing the adapter when it is not in use. Because many piston syringes are made of inexpensive, disposable materials such as plastic, it is desirable that the syringe provide a connector that is integrally formed therewith which may also be disposable.

In light of the aforementioned deficiencies, it is an object of the present invention to provide a new piston syringe which has a handle that permits a user to manipulate the syringe with only one hand both, for discharging and collecting fluids.

Another object of the present invention is to provide a piston syringe having a handle adapted for single handed manipulation which will provide a stable support for the syringe in a substantially inverted position.

Another object of the present invention is to provide a handle for the syringe piston which will support the syringe in an inverted position when the syringe has been filled with fluid.

Yet another object of the present invention is to provide an inexpensive piston syringe which may include an integrally molded tube adapter or other syringe accessory.

A further object of the present invention is to provide a piston syringe in which a tube adapter may be easily stored when not in use.

SUMMARY OF THE INVENTION

The above and further objects and advantages of the present invention are achieved in the embodiment described herein by the provision of a syringe for manually regulating the discharge or collection of fluids which has a substantially cylindrical syringe body and a piston that is slidably received therein. The syringe body has an inner sidewall which defines a hollow barrel extending lengthwise within the syringe body. The syringe body has a first end which defines an opening that leads to the barrel and a second end from which a nozzle extends which has an aperture that is relatively smaller than the barrel. The nozzle permits fluids to communicate in and out of the barrel. The syringe body includes a plurality of flanges that extend outwardly adjacent the open end of the syringe body which are of suitable size for being manually engaged by the fingers of a user of the syringe. The piston passes through the open end of the syringe body and has a longitudinal shaft and first and second ends. A gasket is attached to the first end of the piston for slidably engaging the sidewalls of the hollow barrel to form a seal that is impermeable to fluids at relatively low pressures. A ring having inner and outer surfaces extends from the second end of the piston and defines an opening transverse to the longitudinal shaft of the piston which may be engaged by the thumb of a user of the syringe. Thus, a user may selectively urge the piston into or away from the barrel by manually applying pressure to the ring and to the flanges attached to the syringe body. The ring includes a relatively flattened segment which can support the syringe in an inverted position when it is placed on a substantially horizontal surface. Also, a pair of arms extend between the second end of the piston and the ring to define an area which may receive a syringe accessory such as a tube adapter for use with the nozzle of the syringe. The tube adapter may be frangibly connected to the arms and may be removed by twisting or application of pressure. When the tube adapter has been broken away from the frangible connection and is not in use, a hole is provided in the piston for removably receiving the adapter for storage.

BRIEF DESCRIPTION OF THE DRAWINGS

The foregoing and other objects, advantages and features of the invention, and the manner in which the same are accomplished, will become more readily apparent upon consideration of the following detailed description of the invention taken in conjunction with the accompanying drawings which illustrate a preferred and exemplary embodiment, and wherein:

FIG. 3 is a partial cross-sectional view of the piston syringe shown in FIG. 1 which illustrates the syringe filled with fluid and resting in an inverted position upon a substantially horizontal surface;

FIG. 4 is an partial cross-sectional, detailed view of the nozzle and tube adapter of the present invention; and FIG. 5 is a cross-sectional view taken along line 5—5 of FIG. 2.

DESCRIPTION OF THE PREFERRED EMBODIMENT

Figures 1, 2:
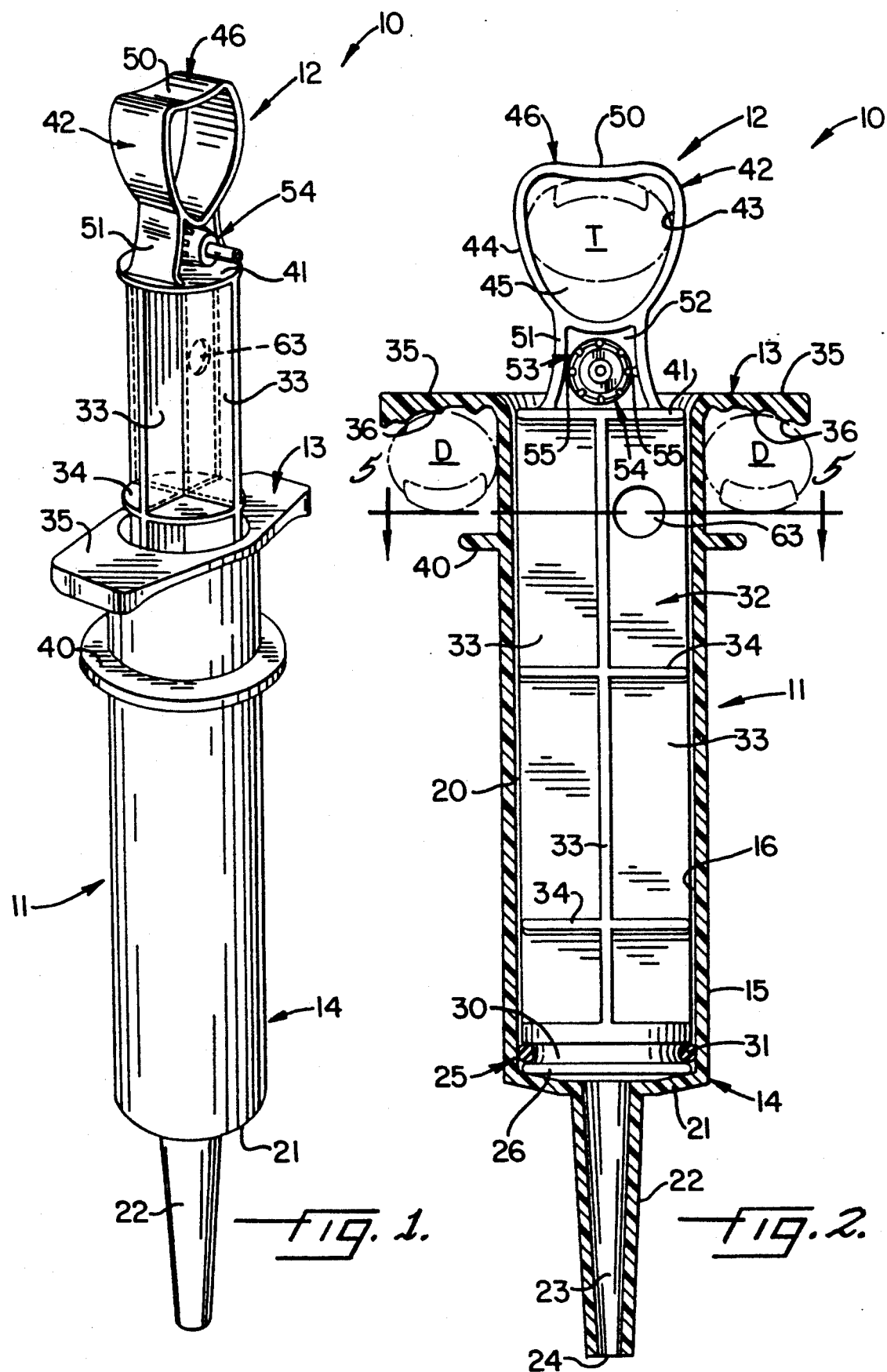
FIG. 1 is a perspective view of one preferred embodiment of a piston syringe made in accordance with the present invention.
FIG. 2 is a partial cross-sectional view of the piston syringe shown in FIG. 1 which illustrates a user gripping the syringe.

Referring now to the drawings, FIG. 1 illustrates a piston syringe made in accordance with the present invention, as indicated generally at 10. The syringe 10 includes a substantially cylindrical syringe body 11 and a piston 12 that is received therein. As illustrated in FIG. 1, the syringe body 11 includes a first end 13 which defines an opening and a second end 14. The syringe 10 may be made of any suitable material, although it has been found to be particularly desirable that the syringe 10 be fabricated of a molded plastic material. It has also been found to be desirable that the syringe be made of a relatively inexpensive material that may be disposable or recyclable.

The syringe body 11 includes an outer sidewall 15 and an inner sidewall 16. The substantially open first end 13 defines an opening that leads to a hollow barrel 20 which is defined by the inner sidewall 16. The hollow barrel 20 extends lengthwise within the syringe body 11. The second end 14 of the syringe body 11 includes a bottom wall 21 from which a concentrically placed nozzle 22 extends. In the preferred embodiment, the nozzle 22 is generally frustoconical in shape and has a relatively smaller aperture 23 extending through its length to permit fluids to communicate between the opening 24 of the nozzle 22 and the interior of the hollow barrel 20. Thus, fluids may communicate with the hollow barrel 20 through the nozzle 22.

The syringe body 11 and piston 12 have generally concentric, longitudinal axes. The piston 12 is slidably received within the barrel 20 of the syringe body 11. The piston 12 has a first end 25 which includes means for slidably engaging the inner side wall 16 of the hollow barrel 20 to form a seal that is impermeable to fluids at relatively low pressures.

In one preferred embodiment, the first end 25 of the piston 12 includes a piston head 26 that is formed integrally with the remainder of the piston 12. A groove 30 extends circumferentially around the piston 12 adjacent the head 26. In a preferred embodiment, the means for slidably engaging the inner sidewall 16 is a gasket 31 that is received within the groove 30. The gasket 31 may be an o-ring made of rubber, soft plastic or other suitable material. However, other arrangements may be used to form the means for forming a seal with the sidewalls 16. For example, an alternative embodiment uses a rubber plug affixed to the first end 25 of the piston 12 to form the head 26 and the sealing means associated therewith.

The piston 12 includes a longitudinal shaft 32 extending rearwardly from the head 26. In a preferred embodiment, the shaft 32 may be formed of ribs 33 which extend radially from the axis of the piston 12 along its length. As illustrated in cross-section in FIG. 5, four ribs 33, each forming a 90° angle with its neighbor, are used in a preferred embodiment. Referring again to FIG. 2, one or more stiffening discs 34 may be positioned at intervals along the length of piston 12. As illustrated in FIG. 5, the discs 34 may conform substantially to the inner sidewall 16 of the syringe body 11.

The syringe body 11 includes a plurality of flanges 35 extending adjacent the open first end 13. In a preferred embodiment, two said flanges 35 extend on opposite sides of the syringe body 11. As shown in FIG. 2, the flanges 35 extend far enough away from the outer sidewall 15 of the syringe body 11 to permit a user to grasp the flanges 35 with fingers D. Also in a preferred embodiment, the flanges 35 may include a plurality of ridges 36 to provide a secure grip for the fingers D of a user.

Also in a preferred embodiment, a second flange 40 may extend outwardly from the outer walls 15 of the syringe body 11 at a location that is sufficiently spaced away from the flanges 35 to permit a user to place his fingers D between the flanges 35 and 40. In a preferred embodiment, the second flange 40 is concentric with the syringe body 11 and extends uniformly away from the outer sidewall 15.

Referring now to FIGS. 2 and 3, the piston 12 includes a second end 41. A ring 42 extends away from the second end 41 of the piston 12 along the longitudinal axis of the piston 12, away from the ribs 33. The ring 42 has an inner surface 43 and an outer surface 44. The inner surface 43 defines an aperture 45 that is of suitable size for receiving a thumb T of a person using the syringe.

As illustrated in FIGS. 1, 2 and 3, the opening of the aperture 45 extends transverse to the longitudinal axis of the piston 12. Also in a preferred embodiment, the ring 42 includes a flattened segment 46 extending around the ring 42 at its side most distal from the second end 41 of the piston 12 In this embodiment, the outer surface 44 of the ring 42 along the flattened segment 46 is sufficiently wide to support the syringe 10 in an inverted position upon a substantially horizontal surface H with adequate stability, as illustrated in FIG. 3. The flattened segment 46 may include a region 50 that is slightly concave relative to the aperture formed by the ring 42. The concave region 50 may conform to the under surface of a thumb T placed upon the outer surface 44 above the concave region 50.

A pair of arms 51 extend between the ring 42 and the second end 41 of the piston 12. Thus, the arms 51 interconnect the ring 42 and the piston 12, and are spaced apart so as to define an area 52 therebetween that is open in a direction transverse to the longitudinal shaft 32 of the piston 12.

A syringe accessory 53 may be frangibly mounted within the area 52 between the arms 51. In one preferred embodiment, the syringe accessory 53 is a tube adapter 54. As illustrated in FIG. 2, the syringe accessory 53, and particularly the tube adapter 54, may be mounted within the arms 51 by one or more frangible tabs 55 that interconnect the accessory 53 to the arms 51. Thus, the syringe accessory 53 may be integrally molded with the remainder of the piston 12. When a user desires to use the accessory 53, the syringe accessory 53 may be removed by pushing or twisting the accessory 53 to break the frangible tabs 55.

As illustrated in FIG. 4, the tube adapter 54 is substantially hollow and includes a first end 60 having a size suitable for frictionally engaging the nozzle 22 near its opening end 24. The tube adapter 54 may also have a substantially cylindrical extension 61 having an outer diameter of suitable size for being received within the interior of a standard size flexible tubing. The tube adapter 54 may include a plurality of ridges 62 extending along the outer surface thereof to increase the ease of manipulating the adapter 54.

In one preferred embodiment, the tube adapter 54 is a Luer adapter in which the outer diameter of the cylindrical extension 61 is of a suitable size for use with a Luer feeding tube. Alternatively, the adapter 54 may be made suitable for use with a Foley catheter.

As illustrated in FIGS. 2 and 5, one of the piston ribs 33 may include a hole 63 of a suitable size for receiving the tube adapter 54 or other syringe accessory. Thus, when the tube adapter 54 has been broken away from the frangible tabs 55 but is not in use, an operator may place the adapter 54 within the hole 63 for storage. The hole 63 is of suitable size for providing a frictional fit with the outer surface of the adapter 54. As illustrated in FIG. 5, the hole 63 is positioned so that the placement of the adapter 54 within the hole 63 does not impede the slidable motion of the piston 12 within the hollow barrel 20.

FIG. 3 shows that the piston syringe 10 made in accordance with the present invention may be filed with the fluid F such as a saline solution or the like and stood on its end in a substantially inverted position. The syringe 10 is stable in this position due to the flattened segment 46 of the ring 42. In a preferred embodiment, the ring 42 is relatively wide in the direction of the axis of the aperture 45 so as to provide a stable support for the syringe 10.

As shown in FIG. 2, an operator may manipulate the piston syringe 10 in the following manner. To discharge a fluid contained with the barrel 20 the operator grips the flanges 35 with two digits D of his hand. It is contemplated that use of the index and third or ring fingers in these positions is most comfortable, although other fingers may, of course, be used at the user's convenience. The user then places his thumb T within the ring 42. By drawing the fingers D and thumb T closer together, a user of the syringe 10 can urge the piston 12 to slide into the barrel 20 of the syringe body 11, thus forcing any fluid F contained therein out of the opening 24 of the nozzle 22. Alternatively, in lieu of placing the thumb T within the ring 42, a user may, at his discretion, choose to place the thumb T atop the outer surface 44 of the concave region 50 of the ring 42. The piston 12 may then be moved into the barrel 20 with equal facility by depressing the concave region 50 with the thumb T in concert with restraining the syringe body 11 with the fingers D.

In contrast to the above, when a user desires to create a suction force to draw fluids F into the hollow barrel 20, the user's fingers D abut against the second flange 40 and the thumb T, which must be placed within the ring 42, is then moved away from the fingers D. In this way, a user may retract the piston 12 out of the barrel 20 to increase the void within the barrel 20 to create a suction that will draw fluids into the barrel 20. Thus, it is seen that the piston syringe 10 may be readily operated with only one hand both to discharge and collect fluids.

In one embodiment (not illustrated), the syringe body 11 may be inscribed with a plurality of markings to denote the interior volume of the barrel 20 depending on the position of the first end 25 of the piston 12.

In the drawings and specification, there has been disclosed a typical preferred embodiment of the invention. Although specific terms have been employed, they have been used in a generic and descriptive sense only and not for purposes of limitation, the scope of the invention being set forth in the following claims.

What is claimed is:

1. A syringe for controlled discharge and collection of fluids, comprising:
    a syringe body having an inner sidewall which defines a hollow barrel extending lengthwise within said syringe body, said syringe body having a first end which defines an opening that leads to said hollow barrel and a second end defining an extended nozzle with a relatively smaller aperture for permitting a fluid to flow in an out of said hollow barrel;
    a plurality of flanges adjacent said open first end of said syringe body and protruding outwardly therefrom, said flanges being of suitable size for being manually engaged by a user of the syringe;
    a piston having a longitudinal shaft which is slidably received within said hollow barrel of said syringe body, said piston having a first end and an opposite second end, with said first end including means for slidably engaging said sidewalls of said hollow barrel to form a seal that is impermeable to fluids at relatively low pressures;
    a ring extending from said second end of said piston and having inner and outer surfaces, said inner surface of said ring defining an aperture having an opening transverse to said longitudinal shaft of said piston for being engaged by the thumb of a user of the syringe, whereby a user may selectively urge said piston into or away from said barrel by manually applying pressure to said ring and to said flanges, said ring including a flattened segment extending around its side away from said second end of said piston, whereby said flattened segment may support said syringe in an upright position when said ring is placed on a substantially horizontal surface;

a pair of substantially parallel arms extending between said ring and said piston to interconnect said ring and piston, such that said arms, piston and ring define an area that is open transverse to said shaft of said piston; and a tube adapter adapted to be coupled with said nozzle on said syringe body, said tube adapter being frangibly mounted within said area between said arms, such that said tube adapter may be removed from said frangible mounting for use with said nozzle.

2. A syringe as defined in claim 1 wherein said flattened segment of said ring has a region having a slightly concave shape relative to said aperture defined by said ring, whereby a user of the syringe may comfortably urge said piston into said syringe barrel by applying pressure to said outer surface of said ring along said flattened segment.

3. A syringe as defined in claim 1 wherein said tube adapter is a Luer feeding tube adapter.

4. A syringe as defined in claim 1 wherein said tube adapter includes a fitting for receiving a Foley catheter.

5. A syringe as defined in claim 1 further comprising a hole defined in said piston for receiving said tube adapter after it has been removed from said frangible mounting on said arms.

6. A syringe as defined in claim 1 wherein said means for slidably engaging said sidewall of said hollow barrel to form a seal comprises:

a circumferential groove formed in said piston adjacent said first end thereof; and a gasket that is received within said groove which is retained against said sidewall.

7. A syringe as defined in claim 1 wherein said syringe is fabricated from a molded plastic material.

8. A syringe for controlled discharge and collection of fluids, comprising:

a substantially cylindrical syringe body having an inner sidewall which defines a hollow barrel extending lengthwise within said syringe body, said syringe body having a first end which defines an opening that leads to said hollow barrel and a second end defining an extended nozzle with a relatively smaller aperture for permitting a fluid to pass in and out of said hollow barrel;

a plurality of flanges adjacent said open first end of said syringe body and protruding outwardly therefrom, said flanges being of suitable size for being manually engaged by a user of the syringe;

a piston having a longitudinal shaft and first and second ends which passes through said open end of said syringe body and which is slidably received within said hollow barrel of said syringe body;

a gasket attached to said first end of said piston for slidably engaging said sidewalls of said hollow barrel to form a seal that is impermeable to fluids at relatively low pressures;

a ring extending from said second end of said piston and having inner and outer surfaces, said inner surface of said ring defining a hollow receptacle having an opening transverse to said longitudinal shaft of said piston for being engaged by the thumb of a user of the syringe, whereby a user may selectively urge said piston into or away from said barrel by manually applying pressure to said ring and to said flanges;

said ring having a generally flattened segment extending around its side most distal from said piston, whereby said flattened segment will support said syringe in an upright position when said flattened segment is placed on a substantially horizontal surface;

a pair of substantially parallel arms extending between said ring and said piston to interconnect said ring and piston, such that said arms, piston and ring define a hollow area that is open transverse to said longitudinal shaft of said piston; and a tube adapter frangibly mounted within said area between said arms, such that said tube adapter may be removed from said frangible mounting for use with said nozzle.

9. A syringe for controlled discharge and collection of fluids, comprising:

a syringe body having an inner sidewall which defines a hollow barrel extending lengthwise within said syringe body, said syringe body having a first end which defines an opening that leads to said hollow barrel and a second end defining an extended nozzle with a relatively smaller aperture for permitting a fluid to flow in and out of said hollow barrel;

a plurality of flanges adjacent said open first end of said syringe body and protruding outwardly therefrom, said flanges being of suitable size for being manually engaged by a user of the syringe;

a piston having a longitudinal shaft which is slidably received within said hollow barrel of said syringe body, said piston having a first end and an opposite second end, with said first end including means for slidably engaging said sidewalls of said hollow barrel to form a seal that is impermeable to fluids at relatively low pressures;

a ring extending from said second end of said piston and having inner and outer surfaces, said inner surface of said ring defining an aperture having an opening transverse to said longitudinal shaft of said piston for being engaged by the thumb of a user of the syringe, whereby a user may selectively urge said piston into or away from said barrel by manually applying pressure to said ring and to said flanges;

a pair of substantially parallel arms extending between said ring and said piston to interconnect said ring and piston, such that said arms, piston and ring define an area that is open transverse to said shaft of said piston; and a tube adapter adapted to be coupled with said nozzle on said syringe body, said tube adapter being frangibly mounted within said area between said arms, such that said tube adapter may be removed from said frangible mounting for use with said nozzle.

10. A syringe as defined in claim 9 further comprising a hole defined in said piston for receiving said tube adapter after it has been removed from said frangible mounting on said arms.

11. A syringe as defined in claim 9 wherein said tube adapter is a Luer feeding tube adapter.

12. A syringe as defined in claim 9 wherein said tube adapter includes a fitting for receiving a Foley catheter.

* * * * *